United States Patent
Prieschl-Grassauer et al.

(10) Patent No.: US 10,220,055 B2
(45) Date of Patent: Mar. 5, 2019

(54) COMPOSITION EFFECTIVE AGAINST VIRAL CONJUNCTIVITIS

(71) Applicant: NICOX S.A., Valbonne (FR)

(72) Inventors: Eva Prieschl-Grassauer, Vienna (AT); Martina Morokutti-Kurz, Vienna (AT); Andreas Grassauer, Vienna (AT); Sabine Nakowitsch, Vienna (AT); Angelika Bodenteich, Vienna (AT); Marielle König-Schuster, Vienna (AT); Christiane Koller, Seying (AT); Frederic Pilotaz, Valbonne (FR)

(73) Assignee: NICOX S.A., Valbonne (FR)

( * ) Notice: Subject to any disclaimer, the term of this patent is extended or adjusted under 35 U.S.C. 154(b) by 0 days.

(21) Appl. No.: 15/112,778

(22) PCT Filed: Jan. 20, 2015

(86) PCT No.: PCT/EP2015/051015
§ 371 (c)(1),
(2) Date: Jul. 20, 2016

(87) PCT Pub. No.: WO2015/110429
PCT Pub. Date: Jul. 30, 2015

(65) Prior Publication Data
US 2016/0331776 A1    Nov. 17, 2016

(30) Foreign Application Priority Data

Jan. 22, 2014 (EP) .................... 14152188

(51) Int. Cl.
| | | |
|---|---|---|
| *A61K 31/731* | (2006.01) | |
| *A61K 9/00* | (2006.01) | |
| *A61K 9/08* | (2006.01) | |
| *A61K 31/737* | (2006.01) | |
| *A61K 47/02* | (2006.01) | |
| *A61K 47/12* | (2006.01) | |
| *A61K 47/18* | (2017.01) | |
| *A61K 47/26* | (2006.01) | |

(52) U.S. Cl.
CPC .......... *A61K 31/731* (2013.01); *A61K 9/0048* (2013.01); *A61K 9/08* (2013.01); *A61K 31/737* (2013.01); *A61K 47/02* (2013.01); *A61K 47/12* (2013.01); *A61K 47/183* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,277,829 B1 * | 8/2001 | Asero | A61K 9/0048 424/114 |
| 6,551,584 B2 | 4/2003 | Bandyopadhyay et al. | |
| 2011/0059919 A1 | 3/2011 | Grassauer et al. | |
| 2011/0091583 A1 * | 4/2011 | Grassauer | A61K 31/731 424/725 |
| 2012/0058206 A1 | 3/2012 | Grassauer et al. | |
| 2012/0302522 A1 | 11/2012 | Grassauer et al. | |

FOREIGN PATENT DOCUMENTS

| | | | | |
|---|---|---|---|---|
| CN | 102988280 A | * | 3/2013 | ......... A61K 31/4709 |
| EP | 0 424 043 A1 | | 4/1991 | |

OTHER PUBLICATIONS

International Search Report and Written Opinion issued in PCT/EP2015/051015 dated Apr. 21, 2015.
Leibbrandt et al., "Iota-Carrageenan Is a Potent Inhibitor of Influenza A Virus Infection," PLoS ONE, Public Library of Science, US, Dec. 1, 2010, pp. 1-11, vol. 5, Issue 12.
Ludwig et al., "Efficacy of a Carrageenan nasal spray in patients with common cold: a randomized controlled trial," Respiratory Research, BioMed Central Ltd., Nov. 13, 2013, pp. 1-11, vol. 14, No. 124.
Wu et al., "Membrane Cofactor Protein Is a Receptor for Adenoviruses Associated with Epidemic Keratoconjunctivitis," Journal of Virology, The American Society for MicroBiology, Apr. 1, 2004, pp. 3897-3905, vol. 78, No. 8.

* cited by examiner

*Primary Examiner* — Shaojia A Jiang
*Assistant Examiner* — Dale R Miller
(74) *Attorney, Agent, or Firm* — Arent Fox LLP

(57) ABSTRACT

The present invention relates to a pharmaceutical composition for use as a medicament in the prophylactic or therapeutic topical treatment of viral eye infections caused by adenovirus of subtype D or influenza A virus of subtype H7. The composition in its ready-for-use formulation comprises iota carrageenan as an active antiviral ingredient and is substantially free of a metal halide salt or contains no more than 0.5% w/v of a metal halide salt.

14 Claims, 1 Drawing Sheet

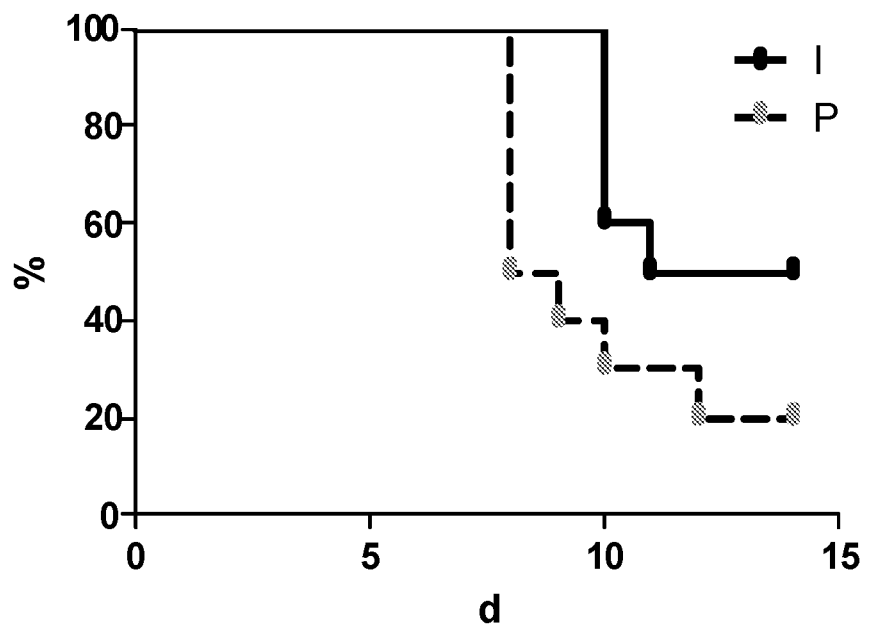

COMPOSITION EFFECTIVE AGAINST VIRAL CONJUNCTIVITIS

CROSS-REFERENCE TO RELATED APPLICATIONS

This application is a National Stage entry of International Application No. PCT/EP2015/051015, filed Jan. 20, 2015, which claims priority to European Patent Application No. 14152188.0, filed Jan. 22, 2014. The disclosure of the prior applications are hereby incorporated in their entirety by reference.

TECHNICAL FIELD

The present invention is in the field of virology and applied medicine and relates to a composition comprising iota carrageenan and their use as a medicament in the prophylactic or therapeutic treatment of viral induced conjunctivitis.

BACKGROUND OF THE INVENTION

Epidemic keratoconjunctivitis (EKC) is a serious and contagious eye infection affecting both the conjunctiva and cornea and is caused by adenoviruses of type D, predominantly of serotypes 8, 19, 37. More than 50 serotypes of adenovirus have been isolated, and at least 19 documented serotypes cause eye infection. The most commonly associated serotypes that cause EKC include adenovirus 8, 19, and 37, and less frequently and in less severe forms, serotypes 2-5, 7, 9, 10, 11, 14, 16, 21, and 29. Because of low levels of natural immunity against adenovirus in the general population, i.e. adenovirus type 8 antibodies are found in less than 5% of the general population in the US, every individual is considered susceptible to infection.

EKC is characterized by typical symptoms of conjunctivitis such as acute onset of watering redness, foreign body sensation and severe pain. Symptoms further include inflammation in the conjunctiva (conjunctivitis) and in the cornea (keratitis), associated pain, edema, diminished eyesight, tearing, sensitivity to light, feeling or sensation as if a foreign body were present in the eye, and the development of pseudo membranes. During the acute phase, which persists for approximately two to three weeks, viruses are present and are replicating. In the typical case, first one eye gets infected after which the infection spreads to the other eye within two to three days. Both eyes are affected in 60% of cases. The infection in the first eye is typically more serious. In approximately 20-50% of patients, corneal opacities are developed that result in deteriorating vision that remains for weeks and months, and in rare cases even years. Since the disease is often epidemic in nature, it is called epidemic keratoconjunctivitis (EKC). Adenovirus conjunctivitis is a reportable infection in Germany (see e.g., Meyer-Rüsenberg et al., Dtsch Arztebl Int 2011; 108(27): 475-80) and is listed as a category IV infectious disease by Japan's National Epidemiological Surveillance of Infectious Diseases (NESID) with mandated collection, analysis and publication of reports on occurrences.

EKC still lacks an effective treatment, hence there is a large unmet medical need. Povidone-iodine eye drops seem to have only limited efficacy and at the same time cause an additional stinging sensation in the inflamed eyes and sometimes even discoloration of the conjunctiva. A more compatible pharmaceutical composition that could be used for the treatment of EKC and for the prevention of its spread would thus be highly desirable for patients suffering from the disease, as well as for individuals that come into contact with such patients such as relatives, friends, colleagues, physicians.

Unlike other influenza virus subtypes that cause predominant respiratory disease in humans, H7 influenza virus infections frequently result in ocular rather than respiratory symptoms (Belser et al., Emerg Infect Dis. 2009; 15:859-865). Therefore it is highly desirable that an antiviral formulation designed for the treatment of viral eye infections is effective during outbreaks of influenza resulting in ocular disease.

The use of carrageenans as excipients and viscosifiers in ophthalmology is well established. U.S. Pat. No. 5,403,841 describes carrageenan-based solutions that are useful for preparing eye drop formulations of pharmaceutically active ingredients. On contact with the tear film the solutions form a gel which maintains extended contact with the conjunctiva, preventing quick removal of the active principle from the eye surface and facilitating its topical delivery. For an extensive review of ophthalmic in situ gelling systems based on carrageenans or other charged polymers see e.g. Rupenthal et al., Int J Pharm. 2011; 411(1-2): 69-77 and 78-85. Polymeric systems containing carrageenan are also useful for trans-scleral delivery of macromolecular agents (Thrimawithana et al., Eur J Pharm Sci. 2011; 44(3):399-409). No intrinsic pharmaceutical activity of carrageenans is mentioned or implied in any of the above-mentioned documents.

Some ocular pharmaceutical preparations that employ carrageenans as excipients and/or mucomimetics contain antiviral agents. For example, international patent application WO 2007/039201 claims photo stable formulations of brivudine to treat herpetic keratitis. It is also known that carrageenans and related anionic polymeric mucomimetics can be used in solutions intended for cleaning and storage of contact lenses, where they improve the astringent properties of said solutions which contain low molecular weight agents with broad antimicrobial activity such as hydrogen peroxide, borate, or cetylpyridinium chloride (see WO 2009/152028 and WO 2010/038129). No antiviral or anti-inflammatory action is attributed to the carrageenan component of these solutions.

Ophthalmic preparations based on natural organic polymers are known to have been designed explicitly for treating conjunctival inflammation. For example, international patent application WO 2005/046562 claims sulfated hyaluronic acids for such a therapeutic purpose. Carrageenans are not mentioned in this disclosure.

Stiles et al. (Invest Ophthalmol Vis Sci 2008; 49(4): 1496-1501) report that treatment of cats suffering from experimentally induced herpetic conjunctivitis with an ocular preparation of lambda-carrageenan reduced the duration of the animal's infectivity, although the clinical course of the conjunctivitis was not shortened. This paper addresses only conjunctival inflammation caused by feline herpes virus; adenoviruses and carrageenans other than those of the lambda class are not mentioned.

In WO 2009/027057 an antiviral effect of iota-carrageenan against B-type (respiratory) adenoviruses was disclosed. In the same application it has been mentioned, however, that no significant effect against subtypes A, C, and D could be determined.

BRIEF DESCRIPTION OF THE INVENTION

It has now surprisingly been found that carrageenan—and in particular iota-carrageenan—can be formulated into a novel pharmaceutical composition to yield antiviral effectiveness against D type adenoviruses and infections caused by said D type adenoviruses, contrary to the state-of-the-art knowledge discussed hereinbefore.

Accordingly, the present invention as claimed in the independent claims relates amongst others to such novel compositions that are deemed useful for the prevention or treatment of epidemic keratoconjunctivitis.

As already reported in WO 2009/027057 iota-carrageenan is not effective against type D adenoviruses under physiological conditions, i.e. when the polymer is dissolved in 0.9% aqueous NaCl solution. However, incidentally it was revealed that when iota-carrageenan is dissolved in water without NaCl the polymer exhibits amazing efficacy against type D adenoviruses.

Further investigation on these unexpected findings resulted in the perception that a reduction of sodium chloride content, as compared to a physiological (0.9%) NaCl solution, in a ready-for-use topical ocular solution can dramatically reduce the $IC_{50}$ values of iota-carrageenan required for activity against H7N7 subtype of influenza A virus. These characteristics allow and recommend using the polymer for the prevention and treatment of infections of the eye caused by H7 influenza A viruses.

It is therefore an object of the present invention to provide for a pharmaceutical preparation comprising carrageenan, preferably iota-carrageenan, for use as a medicament in the prevention or topical treatment of infectious conjunctivitis caused by type D adenoviruses or H7 type influenza A viruses, more specifically for use as a medicament in the prevention or topical treatment of epidemic keratoconjunctivitis caused by adenoviruses and of conjunctivitis occurring in the course of infections with influenza strain H7N7.

DETAILED DESCRIPTION OF THE INVENTION

In a first embodiment, the present invention relates to a pharmaceutical composition that is suitable for the prevention or therapeutical treatment of viral conjunctivitis via administration to an eye affected by or in risk of developing a said viral conjunctivitis. "Viral conjunctivitis" shall mean an infection of the conjunctiva caused by a virus, as defined by code group B30 of the International Classification of Diseases, version 10 (ICD-10).

In some embodiments, the viral conjunctivitis is conjunctivitis or keratoconjunctivitis due to infection by adenovirus (ICD-10 codes B30.1 and B30.0, respectively). In other embodiments, the viral conjunctivitis may be caused by other or unspecified viruses (ICD-10 codes B30.8 and B30.9), and may for example be caused by strain H7N7 of influenza A virus.

In the context of the present invention, the terms "treat" or "treatment" shall mean therapeutic interventions that are intended to modify the clinical course of the viral conjunctivitis in such a way that either clinical symptoms such as ocular redness and pain, disturbances of vision and tear flow, etc., are less severe than without interventions with preparations according to the invention; or that said clinical symptoms persist for shorter periods; or that the time period is shortened during which an infected individual having said symptoms remains capable of transmitting the infectious agents causing viral conjunctivitis to another individual; or any combination of said effects.

Likewise, in the context of the present invention, the terms "prevent" or "prevention" shall mean that either no viral infection occurs or no clinically relevant symptoms of a viral infection occur in a healthy eye that has first been exposed to a preparation according to the present invention and that has subsequently been exposed to an amount of infectious viral agent that would otherwise, i.e. in the absence of such pretreatment, be sufficient to cause viral conjunctivitis. "Partially prevent" shall mean that viral conjunctivitis, if triggered by the infectious viral agent in spite of pretreatment of the eye with a preparation of the present invention, manifests with symptoms that are less severe than without pretreatment, or that show a delayed onset, or that resolve earlier.

In another embodiment, the invention relates to a pharmaceutical composition that prevents or ameliorates late complications of viral conjunctivitis. Such complications are known in the scientific and clinical literature, and include—but are not limited to—corneal opacities, subepithelial infiltrates, and formation of ocular pseudomembranes.

The preparations according to the present invention typically contain carrageenan, preferably iota-carrageenan, as an active antiviral ingredient or as the sole active antiviral ingredient at a concentration of from 0.05% to 1% by weight, preferably of from 0.1 to 0.5%, and most preferably of from 0.1 to 0.3% by weight of the ready-for-use preparation. Also, they are either substantially free from metal halide salts such as sodium or potassium chloride, or contain no more than 0.5% (w/v), preferably no more than 0.1% (w/v) of one or more metal halide salts. Metal halide salts are frequently used in galenic formulations as ionic tonicity adjusting agents. For example, liquid pharmaceutical compositions based on a "physiological" sodium chloride solution usually comprise 0.9% w/v of sodium chloride.

"Substantially free" in this context means that the compositions of the present invention contain no more than trace amounts of metal halide salts possibly originating from impurities of other ingredients present in the composition.

Topically administrable ophthalmic compositions according to the present invention may have a pH value within a range of from 3.5 to 8.0, usually a pH value in the range of from about 4.0 to about 8.0, and an osmolality of about 220 to 320 mOsm/kg. However, for various applications it may be preferable to adjust the osmolality to slightly hypotonic values, said values typically being within a range of from 170 to 250 mOsm/kg, and more specifically within a range of from 190-220 mOsm/kg, in order to compensate for hypertonicity of the tear film due to disease or excessive evaporation with patients suffering from conjunctivitis. According to the present invention adjustment of osmolality is accomplished without the use of ionic tonicity agents, and particularly without the use of metal halide salts such as NaCl or KCl. Instead, the desired osmolality may be adjusted by adding at least one of a low molecular weight sugar and a low molecular weight polyvalent alcohol ("polyol"). Suitable sugars may be selected from the group of monosaccharides, disaccharides, and oligosaccharides, and typically from glucose, fructose, mannose, and sucrose. Suitable polyvalent alcohols, typically short-chain sugar alcohols having a backbone of 3 to 12 carbon atoms, may be selected from the group of glycerol, erythritol, sorbitol, mannitol, xylitol, threitol, inositol, and maltitol.

The topical ophthalmic formulation according to the present invention may comprise one or more ophthalmologically compatible pH adjusting agents or buffer systems that prevent pH drift during storage. Such agents include, but are not limited to, boric acid, sodium borate, potassium citrate, citric acid, sodium bicarbonate, and various inorganic phosphate buffers such as $Na_2HPO_4$, $NaH_2PO_4$, $KH_2PO_4$, and mixtures thereof. The minimal ionic strengths introduced by any such pH-adjustment agents do not interfere with the essence of the invention.

Also, the topical ophthalmic formulation of the present invention may comprise one or more ophthalmologically compatible surfactants. The surfactant facilitates the spread of the formulation across the surface of the eye, and may be non-ionic or anionic. Exemplary non-ionic surfactants include tyloxapol, polyoxyethylene sorbitan esters, polyethoxylated castor oils, poloxamers, polyoxyethylene/polyoxypropylene surfactants, polyoxyethylene stearate, polyoxyethylene propylene glycol stearate, hydroxyalkylphosphonate, lauric or palmitic acid esters and ethers, triethanol amine oleate, or a combination of the foregoing agents, or other agents known to those skilled in the art. The surfactant when included is typically present at a concentration of between 0.02% (w/v) and 0.1% (w/v) of the composition.

In some embodiments, the present topical ophthalmic formulation may contain one or more preservatives to inhibit microbial growth and to prolong shelf life. Exemplary preservatives include, but are not limited to, benzalkonium chloride, disodium edetate (EDTA), polyquaternium-1, polyhexamethylene biguanide, and perborate. The preservative amount is typically less than about 0.01% (w/v) of the total composition.

In addition to the ingredients above, it is contemplated that a variety of additional or alternative ingredients may be present in the pharmaceutical compositions of the present invention, which alternative ingredients include without limitation anti-oxidants such as vitamin E or its commercially available derivatives such as tocopherol polyethylene glycol 1000 succinate (TPGS), ascorbic acid, or sodium metabisulfite.

Another embodiment of the present invention refers to ophthalmic pharmaceutical compositions for topical administration comprising iota carrageenan as active antiviral ingredient in an antiviral effective amount, ethylenediaminetetraacetic acid disodium salt dihydrate (EDTA), an osmolality adjusting agent selected from mannitol or sorbitol, a pH adjusting agent or buffer system and water, with the proviso that the composition in its ready-for-use formulation contains no more than 0.5% w/v of a metal halide salt.

The composition of the above embodiment contains iota-carrageenan at a concentration of from 0.05% to 1% by weight of the ready-to-use preparation, preferably of from 0.1 to 0.5%, preferably of from 0.1 to 0.4% by weight, most preferably of from 0.2 to 0.4% by weight of the ready-for-use preparation.

The ethylenediaminetetraacetic acid disodium salt dihydrate (EDTA) is present at concentrations of 0.05% to 0.2% (w/v), and preferably it is present at a concentration of 0.1% (w/v).

The pH adjusting agents or buffer systems include, but are not limited to, boric acid, sodium borate, potassium citrate, citric acid, sodium bicarbonate, and various inorganic phosphate buffers such as $Na_2HPO_4$, $NaH_2PO_4$, $KH_2PO_4$, and mixtures thereof, preferably a mixture of $Na_2HPO_4$/citric acid.

The ophthalmic pharmaceutical compositions according to this embodiment have a viscosity in the range of 10 to 50 mPa·s, pH value within a range of from 6 to 8.0, and an osmolality of in the range of 280 to 320 mOsm/kg.

Another embodiment of the present invention refers to ophthalmic pharmaceutical compositions comprising iota carrageenan as active antiviral ingredient in a concentration of 0.2% to 0.4% by weight of the ready-to-use preparation, ethylenediaminetetraacetic acid disodium salt dihydrate (EDTA) at a concentration of 0.1% (w/v), mannitol or sorbitol at a concentration in the range of 3% to 4% by weight and a mixture of $Na_2HPO_4$/citric acid, with the proviso that the composition in its ready-for-use formulation contains no more than 0.5% w/v of a metal halide salt.

The ophthalmic pharmaceutical compositions according to this embodiment have a viscosity in the range of 10 to 50 mPa·s, pH value within a range of from 6 to 8.0, and an osmolality of in the range of 280 to 320 mOsm/kg.

Unexpectedly, the presence of EDTA modulates the viscosity of the topical ophthalmic composition comprising iota-carrageenan; in particular EDTA reduces the viscosity of the composition that rises as the amount of iota-carrageenan increases.

This effect of the EDTA allows preparing topical ophthalmic compositions that have a high concentration of iota-carrageenan and an appropriate viscosity to ensure that the compositions are comfortable for the patients and not blurring vision.

Another effect of the presence of the EDTA is that formulations containing EDTA have higher antiviral activity than correspondent formulation without EDTA.

An advantage of the above reported ophthalmic compositions is that infected human eye has high tearing rate and, in general, topical applied therapies are washed out very fast, therefore formulations having high concentration of iota-carrageenan allow to conveying an effective dose of iota-carrageenan to the infected eye.

The pharmaceutical compositions according to the present invention are typically provided in sterile form for topical administration to the frontal part of the eye, and are preferably adjusted for self-administration by the individual in need thereof. In one embodiment, the formulation is a particle-free eye drop. Various containers are known in the art that are suitable for dropwise dispensing of liquids to the ocular surface through a nozzle in a fashion that can be easily controlled by an individual during self-administration of said drops. Preferably, a typical container+nozzle system is designed to maintain sterility of the eye drops during repeated use.

Other galenic formulations within the scope of the invention include ophthalmologically acceptable swabs, ointments, or gels that can be applied to the eye as sprays or aerosols, or gels that can be administered into the conjunctival sac. For each of these formulations various products or application systems are known in the art that are designed to dispense such formulations to the front of the eye without risking mechanical damage to the ocular surface.

For special applications the present pharmaceutical compositions may also be formulated into controlled release devices that are either transiently placed into the conjunctival sac, or dissolve in situ while they release the carrageenan preparation according to the invention.

BRIEF DESCRIPTION OF THE DRAWINGS

FIG. 1 is a graphical representation of the test results of example 6, wherein the antiviral effect of iota-carrageenan was tested on the survival of mice infected intraocularly with avian influenza virus A/H7N7; 10 mice per group were infected with influenza A/turkey/Germany/R11/01 H7N7 and treated over a period of ten days, twice a day with the pharmaceutical composition described in Example 4 or with a placebo, respectively. Therapy was started immediately after infection.

On the x-axis the survival time (days) and on the y-axis the % of surviving mice is given; I=iota carrageenan preparation (black line); P=placebo (dashed line).

EXAMPLE 1

Procedure for Determination of $IC_{50}$ Values for Adenoviruses

A549 cells were seeded into 96 well plates with a cell density of $1.7*10^4$ cells per well and cultivated for 24 hours in a standard DMEM tissue culture medium containing 4.5 g/l glucose. A virus suspension containing varying amounts of carrageenan polymer and NaCl was prepared and incubated for a minimum period of 20 minutes. Cells were infected with the virus suspension containing the test substance (=carrageenan polymer) at a given concentration and at a virus titer of $1.3*10^3$ infectious units per well. One hour after infection the virus inoculum was removed and a semi-liquid overlay containing 2.5% w/v carboxymethyl cellulose (CMC), the carrageenan polymer and the NaCl salt concentration in the amount to be tested was added. The cells were incubated for 5 days at 37° C. Subsequently, the supernatant was removed, cells were washed 3 times with PBS and fixed for immunostaining with an ice cold methanol/acetone (1:1) mixture. Cells were further incubated for 45 min with blocking buffer (Biolegend) and incubated with a mouse anti-adenovirus antibody at a dilution of 1:1000. After incubation for 1 hour the cells were again washed 3 times with a washing buffer containing 0.1% Tween 20 and then incubated for 1 hour with an HRP conjugated anti-mouse IgG antibody at a dilution of 1:1000. Subsequently the cells were washed 3 times with PBS, whereafter TMB substrate (Biolegend) was added. After a reaction time of 10 minutes the reaction was stopped by adding 1N sulfuric acid.

The absorbance was measured at 450 nm. The absorbance of untreated infected cells was set to 100% while the absorbance of uninfected treated cells was set to 0%. Calculation of $IC_{50}$ values was performed with standard fitting software ExcelFit. In parallel, the effect of the procedure on uninfected cells was determined by staining and fixing the cells with crystal violet solution containing 4% formaldehyde. No significant negative effect of the polymer and the different tested salt concentrations on the uninfected cells was detected.

TABLE 1

$IC_{50}$ values of iota-carrageen on three types of adenoviruses are dependent on the concentration of NaCl. All values in µg/ml.
[MA = mannitol]

|  | 0.9% NaCl | 0.5% NaCl | 0.2% NaCl | 0% NaCl | 0% NaCl + 200 mOsm/L MA |
|---|---|---|---|---|---|
| AdV 8 | >200 | 199 | 72 | 38 | 56 |
| AdV 19 | >200 | 76 | 42 | 29 | 36 |
| AdV 37 | >200 | 195 | 37 | 29 | 69 |

As shown in table 1 iota-carrageenan is not effective against adenoviruses 8, 19, and 37 when sodium chloride is present at physiological concentrations. At a concentration of 0.5% NaCl antiviral effectiveness is detectable. In the absence of NaCl the $IC_{50}$ of iota-carrageenan is between 29 and 38 µg of iota-carrageenan per 1 ml of the experimental overlay solution.

The antiviral effectiveness is retained when mannitol is added until an osmolarity of 200 mOsmol/L is reached (0% NaCl+200 mOsm/L MA). For achieving the results shown in Table 1 mannitol was added at a concentration of 36.4 mg/ml to a solution containing 1.2 mg/ml iota-carrageenan, corresponding to an osmolality of 193 mOsm/kg.

EXAMPLE 2

Procedure for the Determination of 1050 Values for Influenza A Virus H7N7

The assay was performed on MDCK cells in a setup with prophylactic pre-incubation of virus and experimental test sample, infection of the cells and post infection treatment using a semi-liquid overlay medium with 2.25% carboxymethylcellulose (CMC). The assay matrix was composed of medium and sample matrix in a ratio of 2:1, resulting from the initial 1:3 dilution of the stock solutions.

The assay was set up in 6 replicates for each test sample concentration, and for infected and uninfected control. Mock infection (toxicity control) was done in triplicates. Final iota-carrageenan concentrations were 400, 120, 36, 10.8, 3.2, 0.97, 0.3, 0.09 µg/ml (1:3.33 serial dilutions). $1.7 \times 10^4$ cells were seeded in 96 well tissue culture plates so that they would reach approx. 90% confluence 24 to 28 hours later. Equal volumes of double concentrated virus dilution and double concentrated test sample dilution series were mixed and incubated at room temperature for 10 minutes. Virus w/o test sample and medium only was added to infected and uninfected control, respectively. Plates were incubated at room temperature for 45 minutes. Then the inoculum was diluted and dispensed in 1 ml aliquots to 5 ml round bottom tubes, preparing 1 tube for each test sample concentration. 4 ml CMC medium per assay plate were transferred to a 50 ml conical tube to prepare the overlay medium for infected and uninfected controls.

Stock solutions were diluted to 800 µg/ml iota-carrageenan with assay medium supplemented with trypsin, yielding a mix of medium and sample matrix in a ratio of 1:2 with trypsin 1:500. Subsequent serial dilutions were performed keeping matrix conditions fixed. 1 ml test sample dilution was added to 1 ml CMC medium and vortexed vigorously. CMC medium for infected/uninfected controls was combined with an equal volume of a mix of assay medium and matrix 1:2 containing trypsin 1:500 and mixed vigorously. Overlay media were kept at 37° C. in a water bath. Shortly before use the solutions were vortexed briefly and poured into the wells of a deep well plate. Final overlay medium: Opti-Pro with 4 mM L-glutamine, ABAM, trypsin 1:1000 and 2.25% CMC. The same procedure was performed in the absence of the virus as a toxicity control.

For immunostaining overlay medium was diluted with 100 µl PBS and aspirated. 100 µl PBS was added to each well. Plates were subjected to a short vigorous agitation on a microplate shaker at maximum speed before PBS was aspirated. The washing was repeated twice or more often if CMC crystals were still resting on the cell layer. 100 µl cold methanol/acetone fixative was added, plates were incubated for 20 to 30 minutes at −20° C., and were left to dry after removal of the fixative.

Following 1 hour incubation with 100 µl blocking buffer, plates were washed once with PBS and incubated with 50 µl antibody dilution (anti-NP 1:500) for 1 hour at room temperature. Detection antibody was added after washing (dilution 1:1000), and kept in contact for 1 hour at room temperature, whereafter the plates were emptied and again washed three times with wash buffer and once with PBS. 100 µl substrate was added. 6 wells w/o (=without) cells were filled with substrate and served as blank. After 10 to 15 minutes the reaction was stopped with 100 µl 1N sulphuric acid. 100 µl were transferred to 96 well flat bottom plates and the absorbance measured at 450 nm.

Evaluation: The mean of blank samples was subtracted from all measured values and means of 6 replicates calculated (raw data). Means of not infected samples was subtracted from all measured values. Values were normalized to the mean of infected samples, and the resulting values subtracted from 100 to yield inhibition as percent of not infected samples. In a diagram, inhibition and blank corrected raw data were plotted against the concentration of iota-carrageenan dilution. The $IC_{50}$ values were calculated as described above for adenoviruses.

TABLE 2

$IC_{50}$ values of iota-carrageenan on influenza H7N7 virus are dependent on the concentration of NaCl. All values in µg/ml [MA = 200 mOsm/L mannitol]

| | 0.9% NaCl | 0.5% NaCl | 0.2% NaCl | 0% NaCl | 0% NaCl + MA |
|---|---|---|---|---|---|
| H7N7 | >50 | 3.5 | 1.9 | <0.09 | <0.09 |

EXAMPLE 3

Antiviral Eye Drops Preparation for the Treatment of Eye Infections
    Iota-carrageenan: 2.4 mg/ml
    Mannitol: 36.4 mg/ml
    Osmolarity: 200 mOsm/L (osmolality: 192 mOsm/kg)
    Viscosity: 76 mPa·s
    Water ad 100%

EXAMPLE 4

Antiviral Formulation of Eye Drops for the Treatment of Eye Infections
    Iota-carrageenan: 1.2 mg/ml
    Mannitol: 36.4 mg ml
    Osmolarity: 200 mOsm/L (osmolality: 193 mOsm/kg)
    Viscosity: 8-15 mPa·s
    Water ad 100%

EXAMPLE 5

A male volunteer was suffering from keratoconjunctivitis for approximately 10 consecutive days. The patient reported redness of the eyes, increased flux of tears, itching and burning of both eyes most likely caused by a viral infection. The volunteer was treated with the eye drops solution of Example 3 at a dosage regime of 5 drops per eye 3 times a day for 5 days. Already after the first day the volunteer reported a reduction of symptoms such as itching and redness. The pathological condition continuously improved during therapy and on day 5 the therapy was discontinued due to complete absence of clinically relevant symptoms. No relapse occurred within an observation period of 14 days.

EXAMPLE 6

Antiviral Effect of Iota-Carrageenan on Mice Infected Intracorneally with Avian Influenza Virus A/H7N7

The H7N7 type of influenza virus predominately enters the body via infection of the eyes. The H7N7 type has been shown to be highly pathogenic to humans and mice. In the worst case, lethal consequences could ensue if the virus spreads from the primary location of infection to the lung. In C57BL6 mice the intraocular infection with influenza virus H7N7 A/turkey/Germany/R11/01 results in a lethal outcome. This model was used to test the pharmaceutical composition described in example 4.

Three weeks old C57BL6 mice (10 per group) were infected intraocularly with 5 µl suspension containing 1.5× $10^5$ plaque forming units (pfU) of influenza virus H7N7 A/turkey/Germany/R11/01. Therapy was started immediately after the infection either with a placebo preparation containing 36.4 mg/ml mannitol or with the preparation described in example 4. Mice were treated over a period of ten days, twice a day with the iota-carrageenan preparation or placebo, respectively. After 14 days 80% of the placebo treated mice had died. In contrast, 50% of the iota-carrageenan treated mice had survived and recovered from the infection (see FIG. 1). A statistical evaluation with a Log-rank test (Prism 5 version 5.02) revealed a significant difference between the two groups with a p-value of 0.0492. Hence it can be concluded that intraocular treatment of mice with an iota-carrageenan preparation as described in example 4 results in a significant effect in survival of mice infected intraocularly with a lethal dose of influenza H7N7 virus.

EXAMPLE 7 (F2)

Antiviral Eye Drops Preparation for the Treatment of Eye Infections
    Iota-carrageenan: 2.4 mg/ml
    Mannitol: 23.50 mg/ml
    $Na_2HPO_4$: 3.67 mg/ml
    Citric acid: 0.46 mg/ml
    Ethylenediaminetetraacetic acid disodium salt dihydrate (EDTA): 1 mg/ml
    Water ad 100%
    Osmolarity: 195 mOsm/kg
    Viscosity: 7.9 mPa·s
    pH=6.8

EXAMPLE 8 (F4)

Antiviral Eye Drops Preparation for the Treatment of Eye Infections
    Iota-carrageenan: 2.4 mg/ml
    Mannitol: 38.4 mg/ml
    $Na_2HPO_4$: 3.67 mg/ml
    Citric acid: 0.46 mg/ml
    Ethylenediaminetetraacetic acid disodium salt dihydrate (EDTA): 1 mg/ml
    Water ad 100%
    Osmolarity: 291 mOsm/kg
    Viscosity: 12.4 mPa·s
    pH=6.70

EXAMPLE 9 (F4S)

Antiviral Eye Drops Preparation for the Treatment of Eye Infections
    Iota-carrageenan: 2.4 mg/ml
    Sorbitol: 40.0 mg/ml
    $Na_2HPO_4$: 3.67 mg/ml
    Citric acid: 0.46 mg/ml
    Ethylenediaminetetraacetic acid disodium salt dihydrate (EDTA): 1 mg/ml
    Water ad 100%
    Osmolarity: 291 mOsm/kg Viscosity: 15.7 mPa·s
pH=6.79

EXAMPLE 10 (F5D)

Antiviral Eye Drops Preparation for the Treatment of Eye Infections
Iota-carrageenan: 3.20 mg/ml
Mannitol: 38.4 mg/ml
$Na_2HPO_4$: 3.67 mg/ml
Citric acid: 0.46 mg/ml
Ethylenediaminetetraacetic acid disodium salt dihydrate (EDTA): 1 mg/ml
Water ad 100%
Osmolarity: 290 mOsm/kg
Viscosity: 44.8 mPa·s
pH=6.77

EXAMPLE 11 (F5S)

Antiviral Eye Drops Preparation for the Treatment of Eye Infections
Iota-carrageenan: 3.2 mg/ml
Sorbitol: 40.0 mg/ml
$Na_2HPO_4$: 3.67 mg/ml
Citric acid: 0.46 mg/ml
Ethylenediaminetetraacetic acid disodium salt dihydrate (EDTA): 1 mg/ml
Water ad 100%
Osmolarity: 289 mOsm/kg
Viscosity: 43.6 mPa·s

EXAMPLE 12

General Procedure for the Preparation of the Formulations

Iota-carrageenan was dissolved in water under constant stirring to yield solutions of 2.4 mg/ml. Then all other compounds were added and dissolved under constant stirring. The final solutions were heated to approx. 80° C. and sterile filtered through a 0.22 µm cellulose acetate membrane with a glass fiber pre-filter.

Measurement of Viscosity of Formulations

The viscosity was determined using a viscosimeter Rheoplus/32 V3.40 21004590-33024. The analyses were performed by two different measurements per sample, each including three recording time points (20, 40 and 60 seconds).

EXAMPLE 13

Evaluation of the Antiviral Activity Against Adenoviruses 8 and 19 (AdV8 and AdV19) of Formulations of Examples 7-11

The antiviral activity of formulations 7-11 was tested by in-vitro replication inhibition of AdV8 and AdV19.

A549 cells were infected with AdV in the presence of (f2), (f4), (f4S), (f5) and (f5S) formulations and further incubated for 5 days, with a semi-fluid overlay containing the tested formulation. Infection was done in presence of 50% and incubation in presence of 17% respective formulation matrix. The inhibition of virus replication was evaluated by the relative amount of AdV protein detected by immunostaining.

The assay was performed in 96 well plates with 5 replicates for each test sample dilution and infected and not infected control. Virus and sample dilutions were incubated in 100% respective placebo and diluted with medium before the mix was added to cells for infection. Post infection culture medium consisted of 17% respective placebo in DMEM with ABAM and 2% FBS and was supplemented with 2.5% CMC (high glucose with L-glutamine (DMEM) with 10% Fetal Bovine Serum (FBS)). Iota-carrageenan concentrations ranged from 400 to 2.3 µg/ml (dilution 1:1.77).

5 days post infection the inhibition of virus replication was evaluated by the relative amount of generated AdV protein detected by immunostaining A toxicity control with uninfected cells was done in parallel.

Cells:
$1.7 \times 10^4$ cells were seeded to 96 well tissue culture plates 24 hours before the assay.

Test Sample Dilution:
A 4-fold concentrated 1:1.77 dilution series of test samples were prepared the respective placebo.

Prophylactic Treatment and Infection:
An aliquot of the virus stock was thawed in cold tap water and briefly agitated on a vortex. A 4-fold concentrated virus was prepared in respective placebo.

Equal volumes of 4-fold concentrated serial diluted test sample or the respective placebo (for positive control=infected, negative control=not infected) and 4-fold concentrated virus dilution were mixed and incubated at RT for 30 minutes. Virus and sample mix or placebo (infected, not infected controls) were diluted with an equal volume of DMEM+ABAM+2% FBS. Equal volumes of sample dilution and particular matrix were mixed for toxicity control.

Cells were washed with medium+ABAM w/o FCS before 30 µl virus (1500 (AdV8) or 1300 (AdV19) TCID50)/ sample mix, virus only (infected, inf) or matrix w/o virus (not infected, ni), or sample w/o virus (tox) were added to the cells. Assay matrix was 50% placebo in DMEM with ABAM and 2% FBS. Plates were incubated for 1 hour at 37° C. Then the inoculum was diluted with 1000 µl medium+ABAM+2% FBS and aspirated.

Post Infection Treatment:
Overlay medium was prepared by combining equal volumes of double concentrated serial diluted test sample or dilution medium (infected, not infected control). Cells were incubated with 100 µl overlay medium at 37° C. for 5 days.

Immunostaining:
Overlay medium was diluted with 100 µl PBS (Dulbecco's PBS w/o Ca, Mg) and aspirated. Plates were washed twice with 100 µl PBS by a short agitation with 900 rpm on a microplate shaker. Residual liquid was removed by tapping plates on a paper towel, before 100 µl cold methanol/acetone mixture was added to cells. Plates were incubated for 20 to 30 minutes at −20° C. Then the fixative was aspirated and plates were left to dry.

Following 45 minutes incubation with 100 µl blocking buffer, plates were washed once with wash buffer and subsequently incubated with 50 µl antibody dilution (1:1000 in wash buffer) for 1 hour at RT. Then the plates were emptied and washed three times with wash buffer before the detection antibody was added (dilution 1:1000 in wash buffer). After 1 hour at RT the plates were emptied and washed twice with wash buffer and twice with PBS. 100 µl substrate was added. 6 wells w/o cells were filled with substrate and served as blank. After 10 minutes the reaction was stopped with 100 µl 1N sulphuric acid. 100 µl were transferred to 96 well flat bottom plates and the absorbance measured at 450 nm.

The absorbance of untreated infected cells was set to 100% while the absorbance of uninfected treated cells was set to 0%. Calculation of $IC_{50}$ values was performed with standard fitting software ExcelFit.

On the bases of the inhibition curves the concentration of iota-carrageenan necessary to reach 50% virus inhibition ($IC_{50}$) were calculated for the tested formulations, the results are summarized in Table 3.

TABLE 3

Calculated $IC_{50}$ values of iota-carrageen on AdV 8 and AdV 19

| Formulation | AdV8 | | AdV19 | |
| --- | --- | --- | --- | --- |
| | $IC_{50}$ (µg/ml) | 95% CI | $IC_{50}$ (µg/ml) | 95% CI |
| Example 7 (f2) | 2.2 | 1.3-3.1 | 3.5 | 1.5-10.7 |
| Example 8 (f4) | 3.0 | 1.4-4.6 | 4.0 | 2.0-6.0 |
| Example 9 (f4S) | 5.8 | 3.9-7.7 | 10.7 | −2.0-23.4 |
| Example 10 (f5d) | 1.4 | −0.7-1.4 | 4.3 | 2.9-5.8 |
| Example 11 (f5S) | 1.0 | −2.2-4.3 | 5.7 | 0.7-10.7 |

95% CI = 95% confidence interval, 95% of the observed confidence intervals will hold the true value of the parameter.

EXAMPLE 14: INFLUENCE OF EDTA ON THE ANTIVIRAL ACTIVITY AGAINST ADV8

The antiviral activity a formulation containing EDTA (f2/EDTA) versus a correspondent formulation without EDTA (f2 w/o EDTA) was compared an in-vitro assay investigating the inhibition of AdV8.

Tested Formulations:
(f2/EDTA):
Iota-carrageenan: 2.4 mg/ml
Mannitol: 23.50 mg/ml
$Na_2HPO_4$: 3.67 mg/ml
Citric acid: 0.46 mg/ml
Ethylenediaminetetraacetic acid disodium salt dihydrate (EDTA): 1 mg/ml
Water ad 100%
(f2 w/o EDTA):
Iota-carrageenan: 2.4 mg/ml
Mannitol: 23.50 mg/ml
$Na_2HPO_4$: 3.67 mg/ml
Citric acid: 0.46 mg/ml
Water ad 100%

The assay was performed according to the procedure described in Example 14 with a slightly adapted protocol.

In this assay set up the virus was incubated for 10 min in the presence of formulations diluted in correspondent placebo with a final concentration of 33% formulation matrix in medium. Accordingly A549 cells were infected with adenovirus (AdV8) in the presence of 17% formulation matrix in medium and further incubated for 5 days with a semi-liquid overlay containing the tested formulation (again 17% formulation matrix in medium). The inhibition of virus replication was evaluated by the relative amount of generated AdV protein detected by immunostaining.

On the bases of the inhibition curves the concentration of iota-carrageenan necessary to reach 50% virus inhibition ($IC_{50}$) were calculated for the tested formulations, the results are summarized in Table 4. The results show that the addition of EDTA in the eye drop formulation resulted in higher antiviral activity than the correspondent formulation without EDTA.

TABLE 4

Calculated $IC_{50}$ values of iota-carrageen on AdV 8

| Formulation | $IC_{50}$ (µg/ml) |
| --- | --- |
| f2/EDTA | 6.0 |
| f2 w/o EDTA | 37.1 |

The invention claimed is:

1. An ophthalmic pharmaceutical composition for topical administration comprising an active ingredient at a concentration in the range of from 0.2 to 0.4% by weight, water, an osmolality adjusting agent selected from mannitol or sorbitol, a pH adjusting agent or buffer system and ethylenediaminetetraacetic acid disodium salt dehydrate (EDTA), wherein the active ingredient consists of iota-carrageenan, and with the proviso that the composition in its ready-for-use formulation contains no metal halide salt selected from the group consisting of sodium chloride and potassium chloride.

2. The composition according to claim 1 wherein the ethylenediaminetetraacetic acid disodium salt dihydrate (EDTA) is present at concentrations of 0.05% to 0.2% (w/v).

3. The composition according to claim 2 wherein the ethylenediaminetetraacetic acid disodium salt dihydrate (EDTA) is present at a concentration of 0.1% (w/v).

4. The composition according to claim 1 wherein the buffer system is a mixture of $Na_2HPO_4$/citric acid.

5. The composition according to claim 1 having a viscosity in the range of 10 to 50 mPa·s, a pH value in the range of 6.0 to 8.0, and an osmolality in the range of 280 to 320 mOsm/kg.

6. The composition according to claim 1 wherein iota carrageenan has a concentration of from 0.2% to 0.4% by weight, ethylenediaminetetraacetic acid disodium salt dihydrate (EDTA) has a concentration of 0.1% (w/v), mannitol or sorbitol have a concentration in the range of 3% to 4% by weight and the buffer system is a mixture of $Na_2HPO_4$/citric acid.

7. The composition according to claim 1, wherein the composition further comprises one ophthalmologically compatible additive selected from the group consisting of a surfactant, an antimicrobial preservative and an anti-oxidant.

8. A composition according to claim 1 in form of eye drops having the following composition:
Iota-carrageenan: 3.2 mg/ml
Sorbitol: 40.0 mg/ml
$Na_2HPO_4$: 3.67 mg/ml
Citric acid: 0.46 mg/ml
Ethylenediaminetetraacetic acid disodium salt dihydrate (EDTA): 1 mg/ml
Water ad 100%.

9. An ophthalmic pharmaceutical composition for topical administration consisting essentially of an active antiviral ingredient at a concentration in the range of from 0.2% to 0.4% by weight, water, 0.1% (w/v) ethylenediaminetetraacetic acid disodium salt dihydrate (EDTA), from 3% to 4% by weight mannitol or sorbitol, and a buffer system which is a mixture of $Na_2HPO_4$/citric acid, wherein the active antiviral ingredient consists of iota-carrageenan, and the proviso that the composition in its ready-for-use formulation contains no metal halide salt selected from the group consisting of sodium chloride and potassium chloride.

10. A method for treating viral eye infections caused by adenovirus of subtype D or influenza A virus of subtype H7 comprising administering to the eye of a subject in need thereof a pharmaceutical composition comprising between 0.2 to 0.4% by weight of an active antiviral ingredient, wherein the active ingredient consists of iota-carrageenan, and with the proviso that the composition in its ready-for-use formulation contains no a metal halide salt selected from the group consisting of sodium chloride and potassium chloride.

11. The method according to claim 10, wherein the composition further comprises an osmolality adjusting agent selected from the group consisting of monosaccharides, disaccharides, oligosaccharides, and low molecular weight polyols.

12. The method according to claim 11, wherein the osmolality adjusting agent is selected from the group consisting of glucose, fructose, sucrose, mannose, glycerol, erythritol, mannitol, sorbitol, inositol, xylitol, threitol, and maltitol.

13. The method according to claim 10, wherein the composition further comprises at least one ophthalmologically compatible additive selected from the group consisting of a pH adjusting agent, a surfactant, an antimicrobial preservative, and an anti-oxidant.

14. The method according to claim 10 comprising administering to the eye of a subject in need thereof a pharmaceutical composition having the following composition:
Iota carrageenan: 3.2 mg/ml
Sorbitol: 40.0 mg/ml
$Na_2HPO_4$: 3.67 mg/ml
Citric acid: 0.46 mg/ml
Ethylenediaminetetraacetic acid disodium salt dihydrate (EDTA): 1 mg/ml
Water ad 100%.

* * * * *